(12) United States Patent
Klewinghaus

(10) Patent No.: US 9,649,421 B2
(45) Date of Patent: May 16, 2017

(54) METHOD FOR INFLUENCING THE PRESSURE WITHIN A HEATING BAG DURING A MEDICAL TREATMENT AND MEDICAL APPARATUS

(71) Applicant: FRESENIUS MEDICAL CARE DEUTSCHLAND GMBH, Bad Homburg (DE)

(72) Inventor: Jürgen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 14/916,495

(22) PCT Filed: Sep. 5, 2014

(86) PCT No.: PCT/EP2014/068974
§ 371 (c)(1),
(2) Date: Mar. 3, 2016

(87) PCT Pub. No.: WO2015/032914
PCT Pub. Date: Mar. 12, 2015

(65) Prior Publication Data
US 2016/0213829 A1    Jul. 28, 2016

(30) Foreign Application Priority Data

Sep. 6, 2013  (DE) .................. 10 2013 014 754

(51) Int. Cl.
*A61M 37/00*  (2006.01)
*A61M 1/16*  (2006.01)
(Continued)

(52) U.S. Cl.
CPC ............ *A61M 1/166* (2014.02); *A61M 1/167* (2014.02); *A61M 1/1664* (2014.02);
(Continued)

(58) Field of Classification Search
CPC .. A61M 1/1654; A61M 1/1656; A61M 1/166; A61M 1/1662; A61M 1/1664;
(Continued)

(56) References Cited

U.S. PATENT DOCUMENTS

2002/0147426 A1* 10/2002 Faries, Jr. ............. A61M 5/445
604/140
2002/0147481 A1  10/2002 Brugger et al.
(Continued)

FOREIGN PATENT DOCUMENTS

| EP | 2366419 A1 | 9/2011 |
|---|---|---|
| WO | 99-02206 A1 | 1/1999 |
| WO | 2005-072666 A1 | 8/2005 |

OTHER PUBLICATIONS

International Search Report from PCT/EP2014/068974, mailed on Nov. 11, 2014.

*Primary Examiner* — Philip R Wiest
(74) *Attorney, Agent, or Firm* — Fish & Richardson P.C.

(57) ABSTRACT

A method for controlling or regulating the pressure, which prevails within a heating bag of a tubing system used for the treatment, wherein the method encompasses the steps: Determining the pressure; comparing the determined pressure with a reference pressure or detecting its state with respect to a reference pressure range and changing a treatment parameter of the treatment of the patient or suggesting a correction of the treatment parameter in case the determined pressure is below or above, respectively, the reference pressure or outside the reference pressure range.

19 Claims, 6 Drawing Sheets

(51) Int. Cl.
*A61M 1/34* (2006.01)
*A61M 5/44* (2006.01)

(52) U.S. Cl.
CPC ............ *A61M 1/342* (2013.01); *A61M 5/445* (2013.01); *A61M 2205/3331* (2013.01); *A61M 2205/36* (2013.01)

(58) Field of Classification Search
CPC .. A61M 1/1668; A61M 1/167; A61M 1/1672; A61M 1/1674; A61M 1/342; A61M 5/445; A61M 2205/3331
See application file for complete search history.

(56) References Cited

U.S. PATENT DOCUMENTS

2007/0066928 A1* 3/2007 Lannoy ................... A61M 1/16
604/6.07
2009/0299273 A1 12/2009 Lee et al.

\* cited by examiner

METHOD FOR INFLUENCING THE PRESSURE WITHIN A HEATING BAG DURING A MEDICAL TREATMENT AND MEDICAL APPARATUS

CROSS REFERENCE TO RELATED APPLICATIONS

The present application is the national stage entry of International Patent Application No. PCT/EP2014/068974, filed on Sep. 5, 2014, the disclosure of which is expressly incorporated herein by reference in its entirety, and which claims priority to Application No. DE 10 2013 014 751.4, filed in the Federal Republic of Germany on Sep. 6, 2013.

FIELD OF INVENTION

The present invention relates to a method for regulating or controlling, during the treatment of the blood of a patient, the pressure which prevails within a heating bag of a tubing system used for the treatment. The present invention further relates to a medical apparatus comprising a control or regulating device which is configured to execute the method.

BACKGROUND

From treating patients by dialysis, devices are known for heating dialysis fluid before the fluid flows into the dialyzer or blood treatment filter in which substances, e.g. blood and dialysis solutions, are exchanged through a membrane which usually is of a semi-permeable type. Some of these heating devices require achieving a secure contact or require keeping a maximum distance between the heating device which may, for example, be shaped as heating coils or heating spindles and a container containing the dialysis fluid to be heated, wherein the container is surrounded by said heating device and wherein the container may, by way of example, be embodied as a bag. With a heating device of this type, heating the dialysis fluid as intended depends on how well the container contacts the heating device, which may, for example, be embodied as a bag heater (or vice versa). This applies to other fluids which are heated in containers as well.

SUMMARY

One object of the present invention is to propose an apparatus and a method for achieving or ensuring a desired or required contact between the heating device and the container containing or comprising fluid, for avoiding a collapse of the container or for avoiding that the distance between the heating device and the container exceeds a maximum volume during use or while the patient is undergoing a treatment.

A method is thus proposed by the present invention for controlling the pressure which prevails during a blood treatment of a patient within a heating bag of a tubing system, used for the treatment, or within a connected medical apparatus.

The method encompasses defining or determining the pressure (or its value) prevailing within the heating bag. It further encompasses comparing the defined or determined pressure with a reference pressure (or with its value) and/or detecting its state with respect to a reference pressure range (or its value range). Furthermore, it encompasses changing a treatment parameter of the treatment of the patient and/or suggesting a correction of the treatment parameter in case the comparison reveals that the determined pressure, depending on the target of the monitoring, is below or above the reference pressure and/or outside of the reference pressure range.

The medical apparatus according to the present invention, comprises, optionally, a tubing system or is connected thereto. It comprises in any case a control or regulating apparatus which is configured to execute the method according to the present invention in at least one of the embodiments of the method described herein.

In all of the following embodiments, the use of the expression "may be" or "may have" and so on, is to be understood synonymously with "preferably is" or "preferably has," and so on, respectively, and is intended to illustrate an embodiment according to the present invention.

Whenever numerical words are mentioned herein, the person skilled in the art shall recognize or understand them as indications of numerical lower limits. Unless it leads the person skilled in the art to an evident contradiction, the person skilled in the art shall comprehend the specification, for example, of "one" always as "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Advantageous developments of the present invention are each subject-matter of dependent claims and embodiments.

Embodiments according to the present invention may have one or several of the features stated as follows.

In some exemplary embodiments according to the present invention, determining the pressure is a detection, an estimation, a conclusion thereof, or a measurement of pressure.

In specific exemplary embodiments according to the present invention, determining is achieved in a direct or indirect manner.

In some exemplary embodiments according to the present invention, determining the pressure is achieved by measuring the filtrate pressure by means of a pressure sensor. The latter may be in fluidic contact with the content of the heating bag.

In specific exemplary embodiments according to the present invention, the parameter of the treatment is a substitution flow (or a substitution rate) or an ultrafiltration rate. Any other treatment parameter, which may effect an increase of pressure, is equally encompassed by the present invention.

In some exemplary embodiments according to the present invention, the substitution flow is reduced so that, or until, the pressure is, or reaches again, below or above, respectively, (i.e. in any case: on the desired side) the reference pressure, and/or within the reference pressure range. A reference pressure range may have an upper and a lower threshold.

In specific exemplary embodiments according to the present invention, the reference pressure corresponds to the ambient pressure.

In some exemplary embodiments according to the present invention, the pressure is determined by a pressure detector which is arranged in a dialysis fluid line downstream of a dialysis fluid pump.

In specific exemplary embodiments according to the present invention, the pressure detector is arranged upstream of a heating device, e.g. in a transmission line.

In some exemplary embodiments according to the present invention, the pressure is influenced by a device, co-effected or amended. The device is selected out of a group which comprises at least a valve, a throttle, and an orifice.

The aforementioned device for influencing the pressure may be arranged upstream of a dialyzer and upstream of a heating device. It may be arranged downstream of a substituate pump.

"Influencing" pressure shall be understood in certain exemplary embodiments according to the present invention as decreasing and/or increasing the pressure by means of the device. Such influence may take place if or when the determined pressure is below or above, respectively, the reference pressure or beyond the reference pressure range.

In some exemplary embodiments according to the present invention, the pressure is determined by a pressure detector, which is arranged in a substitute line downstream of a substitute pump, preferably upstream of a heating device for substitute, e.g., in a transmission line.

In specific exemplary embodiments according to the present invention, the heating bag contains dialysis fluid and/or substituate.

In certain exemplary embodiments of the medical apparatus according to the present invention, it is designed as a blood purification device, e.g., as dialysis apparatus, as filtration apparatus, as diafiltration apparatus or as dialysis apparatus in any other sense known to the skilled person.

The medical apparatus is in certain exemplary embodiments according to the present invention a dialysis apparatus which is particularly configured to be used for the continuous venous hemodiafiltration (CVV-HDF) and/or to be used for the acute dialysis.

In specific exemplary embodiments according to the present invention, the tubing system comprises a tubing adaptor.

The tubing adapter comprises at least one locking mechanism for temporarily or reversibly blocking a flow-through lumen of the tubing adapter or of the tubing section connected thereto, and/or a device for generating or amending a flow resistance.

The dialysis fluid tubing system comprises at least one tubing adapter and/or is integral with (or is an integral part of) such one tubing adapter or comprises at least one locking mechanism for blocking its flow-through lumen and/or a device for generating or amending of the flow resistance.

In some particular embodiments according to the present invention, the flow resistance changes step-wisely and/or not steadily.

In some embodiments according to the present invention, the tubing adapter is in fluid communication with the tubing adapter of the tubing system with which it is connected. Therefore, when being used, the tubing section is being flown-through by the same fluid and/or by the same amount of fluid as the tubing section.

In some embodiments according to the present invention, the flow resistance is generated and/or amended by the tubing adapter or by one of its components.

In some embodiments according to the present invention, the change of the flow resistance takes place within the flow-through lumen of the tubing adapter.

In particular embodiments according to the present invention, the flow resistance is changed according to a pressure drop or causes one.

In some particular embodiments according to the present invention, a flow through the tubing adapter is blocked by the locking mechanism in its blocked state.

In some embodiments according to the present invention, an entry of dialysis fluid from a source of dialysis fluid into the dialyzer is blocked by the locking mechanism in its blocked state. In some particular embodiments according to the present invention, an entry of substituate from a source of substituate into the extracorporeal blood circuit is blocked by the locking mechanism in its blocked state.

In some particular embodiments according to the present invention, a flow through the tubing adapter is impeded by the locking mechanism depending on a pressure prevailing upstream of the tubing adapter, and there in particular downstream of a heating device, for example embodied as a bag heater, by which fluid, e.g., dialysis fluid, guided through the tubing adapter was heated.

In some exemplary embodiments according to the present invention, a flow, or any flow, downstream of the tubing adapter and/or upstream of the tubing adapter is amended or impeded by the device for generating a flow resistance during intended use of the tubing adapter depending on a pressure prevailing upstream of the tubing adapter.

In certain embodiments according to the present invention, the locking mechanism or the device for generating a flow resistance serve to rule out or exclude pre-defined pressures upstream of the tubing adapter. A pre-defined pressure may be in particular a vacuum or negative pressure or a pressure below a pre-defined minimum pressure.

The pre-defined minimum pressure may be defined or set by selecting the particular elements such as a check valve or a pressure stop valve of the tubing adapter.

The terms check valve and pressure stop valve are being used interchangeably in some particular exemplary embodiments according to the present invention whenever this is considered by the skilled person as possible from a technical point of view.

In some particular exemplary embodiments according to the present invention, the minimum pressure is a vacuum or a negative pressure. In certain exemplary embodiments according to the present invention, the minimum pressure is a pressure at which a container or a bag of the actually used bag heater does reliably not collapse if this pressure is applied inside of the container or bag. In specific exemplary embodiments according to the present invention the minimum pressure is the reference pressure.

In some particular exemplary embodiments according to the present invention, the minimum pressure relates to a pressure inside of the container or bag of the bag heater actually used; in other exemplary embodiments according to the present invention, the minimum pressure relates to a pressure inside of the dialysis fluid tubing system between the heating device and dialyzer.

In some exemplary embodiments according to the present invention, neither the tubing adapter nor components thereof are placed in a bypass line for the pump.

In specific exemplary embodiments according to the present invention, the tubing system, particularly the dialysis fluid tubing system, comprises no bypass line for the pump.

In some particular exemplary embodiments according to the present invention, neither the tubing adapter nor its components are devices for limiting a pressure or do not act as such.

In certain exemplary embodiments according to the present invention, the tubing adapter or its components are devices for ensuring a minimum pressure or act as such.

For example, in some particular exemplary embodiments according to the present invention the check valve or the pressure stop valve mentioned herein are not intended to limit a pressure by opening once a sufficiently high pressure has been reached. Rather, it closes once the pressure is too low.

In certain embodiments according to the present invention, the tubing system comprises a tubing section which is intended to be inserted into a pump, for example an occluding pump such as a roller pump.

In some exemplary embodiments according to the present invention, the tubing adapter, its locking mechanism or its device for generating or amending a flow resistance is a valve and/or a throttle and/or an orifice or comprises at least one of the latter elements.

In the case of a valve, it can be for example a check valve or a pressure stop valve having a defined or pre-determined opening pressure.

In certain exemplary embodiments according to the present invention, the opening pressure of the locking mechanism of the tubing adapter is 50 hPa (or mbar) at least and/or 350 hPa at most.

In some exemplary embodiments according to the present invention, the minimum pressure mentioned above is 5 hPa, or it is 5 hPa higher than a pressure which prevails downstream of the tubing adapter or the locking mechanism.

In some particular exemplary embodiments according to the present invention, the device for generating or amending a flow resistance effects an amendment such that during use of the tubing adapter according to the present invention a pressure difference of at least 5 hPa and/or 1000 hPa at most, preferably at least 50 hPa and/or 400 hPa at most, particularly preferably of at least 100 hPa and/or 350 hPa at most, prevails over the device or over the tubing adapter.

In some exemplary embodiments according to the present invention, the tubing system, e.g., the dialysis fluid tubing system, is integral with the tubing adapter or firmly connected to it—meaning for example that the connection can only be released in a destructive manner.

In certain exemplary embodiments according to the present invention, the tubing system, e.g., the dialysis fluid tubing system or the substitute tubing system comprises in addition a container or bag (for example a collecting or storage container) comprising dialysis fluid and/or substituate or is connected thereto. This fluid is intended for flowing through the tubing system or parts thereof. Also, the tubing system may optionally comprise a pump or be connected with a pump arranged in a manner such that it can convey the aforementioned fluid in the lumen of the tubing system. The pump can be embodied as a displacement pump, for example a roller pump.

The container may be embodied as one or more bags. Such bags are disclosed in US 2005/020959 A1, by way of example, the whole content of which is incorporated into the present specification by reference thereto.

In some particular exemplary embodiments according to the present invention, the tubing system comprises a heating device for heating the fluid or is interconnected with it or comprises a section which is intended to be interconnected with a heating device in use.

In specific exemplary embodiments according to the present invention, the heating device is thereby arranged upstream of the tubing adapter.

The heating device may be a type which requires a constant, positive pressure within the interior of the container for achieving the desired heating results.

In some particular exemplary embodiments according to the present invention, the heating device is a bag heater.

In some exemplary embodiments according to the present invention, the tubing system or parts thereof, in particular the dialysis fluid tubing system, are a disposable.

In some particular exemplary embodiments according to the present invention, the dialysis fluid tubing system is a dialysis fluid tubing.

In specific exemplary embodiments according to the present invention, the medical apparatus according to the present invention is a treatment system or a treatment apparatus having an extracorporeal blood circuit and/or a tubing set or system according to the present invention or is connected thereto.

In some particular embodiments according to the present invention, the tubing adapter is connected to the tubing system, e.g., the dialysis fluid tubing system, downstream of a heating device, in particular downstream of a bag heater. The heating device is also connected to the tubing system.

In certain embodiments according to the present invention, the tubing adapter is connected to the dialyzer coupling of the dialysis fluid tubing system. To this end, the tubing adapter may be embodied to be connected to, for example, the one or several dialyzer couplings by plug connections, by plug-screw connections or the like, in particular without using tools or further connecting elements.

The term tubing 'adapter' as used herein is not intended to be construed in a limiting manner such that the tubing adapter was intended to interconnect things that could not be interconnected with each other without the adapter. Rather, the term encompasses also an intermediate element or interconnecting element which is intended to connect two tubing sections of a tubing system or a tubing section to a dialyzer in fluid communication with each other, in particular in a direct manner.

In certain embodiments according to the present invention, the tubing adapter consists of a locking mechanism, which is here exemplarily embodied as a check valve or valve, two tubing connectors as well as two—optionally provided and preferably short—tubing sections of the tubing adapter. The tubing adapter may comprise further components.

In some exemplary embodiments according to the present invention, the particular components of the tubing adapter are firmly connected to each other, for example by bonding or ultrasound welding. However, the components may be releasably connected to each other as well. This would be advantageous in that the tubing adapter could still be provided right before use with tubing connectors of different sizes which mate with the corresponding tubing connectors of other tubing systems.

For connecting the tubing adapter, the tubing connectors are connected with tubing couplings of the tubing system. The tubing connector may be embodied as a first coupling, here also referred to as 'male' part or connector, the tubing connector as 'female' part or connector. In some particular exemplary embodiments, the female part of the coupling is embodied identically to a corresponding tubing connector of the tubing section.

The two tubing connectors are assembled or plugged into each other as coupling such that the tubing system is extended hereby by the uncovered or free length of the tubing adapter.

The valve of the tubing adapter opens—for example against the force of a spring—if or when a minimum pressure prevails upstream of the valve.

In some exemplary embodiments according to the present invention, the dialysis fluid pump and the substitute pump are supplied by a common container or by a common source. This is carried out in some particular exemplary embodiments according to the present invention via a common line.

In certain exemplary embodiments according to the present invention, the dialysis fluid pump and the substitute pump are supplied by separate containers or sources.

In some exemplary embodiments according to the present invention, the fluids conveyed from the bags or sources towards the dialysis fluid pump and the substitute pump, respectively, are first combined or unified by means of a Y-piece, or the fluids flowing out of the two bags or sources are each conveyed through the one and same Y-piece before the fluid or the mixture of the fluids is fed through the common leg of the Y-piece into the inlet line(s).

In certain exemplary embodiments according to the present invention, the inlet lines for conveying fluids to the dialysis fluid pump and to the substitute pump via a connecting line are connected with each other in fluid communication.

In some exemplary embodiments according to the present invention, the Y-piece or the common line leads or extends into the connecting line.

For details about the embodiment and function of the tubing adapter, reference is made to the publication of the German patent application 10 2012 004 673.1 applied for the patent applicant of the present invention on Dec. 3, 2012 at the Deutschen Patent—and Markenamt (DPMA); the disclosure of which is incorporated herein by way of reference.

In specific exemplary embodiments according to the present invention, the medical apparatus according to the present invention comprises all devices required for executing the method according to the present invention, parts or components or it is in signal communication therewith. In this way, a device, preferably of the same name as the corresponding method step, is provided for each one of the method steps according to the present invention, said device being at least suitable, correspondingly connected and/or configured for executing the respective method step. In particular, the medical apparatus may comprise a device for determining the pressure (e.g., a pressure detector), a device for comparing the determined pressure with a reference pressure or defining its state with respect to a reference pressure range (e.g., a comparison device) and a device for changing at least one treatment parameter of the treatment of the patient or suggesting a correction or a change of at least one treatment parameter in case the determined pressure is below or above, respectively, the reference pressure or beyond the reference pressure range (e.g., a correction device).

In some exemplary embodiments according to the present invention, the information, obtained about the pressure prevailing in the heating bag, is used by the present invention to intentionally control (with back coupling) or to regulate (without back coupling) the treatment parameters adjusted or selected by the user, i.e., the medical staff, for the treatment of the patient. This may be carried out in an automated manner, respectively. Alternatively, a proposal may be submitted to the user as how one or several treatment parameters may be modified. An alarm, which may be displayed on a screen by way of example, may be issued to draw the attention of the user to the proposal. The user may accept, reject or modify and subsequently accept the proposal. The aforementioned parameters include at least the substitution flow as well as the (ultra)filtration rate.

In some exemplary embodiments according to the present invention, the heating device comprises no sensors for monitoring and/or detecting or defining the deformation and/or the position of the heating bag, in particular no mechanical or optical sensor, e.g., no push-button switch and/or no movable element set for this purpose.

In some particular exemplary embodiments according to the present invention, the tubing system comprises no tubing adapter.

The medical apparatus according to the present invention may be connected to, or may comprise, a tubing system during the blood treatment of the patient. The tubing system comprises at least a container containing fluid, e.g., dialysis fluid or substituate, which are each provided for flowing through the tubing system. It further comprises at least a pump which is arranged in the tubing system, or it is connected or provided to be connected thereto, respectively, to convey the fluid, e.g., dialysis fluid or substituate. Furthermore, the tubing system comprises, or is connected to, a heating device for heating the fluid. The heating device comprises, or is embodied as, a heating bag containing fluid, e.g., dialysis fluid or substituate.

Some or all of the embodiments according to the present invention may feature one, several or all of the advantages stated above and/or hereinafter.

An alternative arrangement, for example, in the dialysis fluid tubing system would be a pump, for example an occluding pump (e.g., a roller pump), which is arranged downstream of the heating device. The function of the tubing adapter having, for example, a check valve or a pressure stop valve would then be, at least partly, assumed by the occluding pump which could avoid a vacuum or negative pressure between heating device and dialyzer by its occluding effect. An arrangement according to the present invention with a dialysis fluid tubing system in which the heating device, for example a bag heater, is provided downstream of the pump and in which the tubing adapter is provided downstream of the heating device provides for the following advantages compared with the said alternative solution: A vacuum or negative pressure within the heating device may not only be caused by the dialyzer (see the description made with respect to FIG. 1: a high TMP inside the dialyzer may have several reasons) but also by the aspiration or suction of the occluding pump as it is known for roller pumps. The undesired effect of a vacuum or a negative pressure inside the heating device may also be caused by the aspiration or suction effect of the occluding pump that is arranged downstream of the heating device.

Further, errors in the balancing are avoided because the heating device and in particular the bag heater—although being considered as an additional volume storage—is normally not being taken into account in the balancing system. By or having a tubing adapter, changes resulting from vacuum and a collapsing vessel of the heating device, in particular of the bag heater, as it is the case with the alternative solution described above, may advantageously be avoided.

Further, by means of the present invention a warming of the dialysis fluid while the dialysis fluid is not being conveyed as it may happen with an alternative arrangement may be avoided with certain bicarbonate-containing solutions. Such warming may deteriorate the quality of the dialysis fluid. This may result in precipitations of the dialysis fluid.

An undesired cooling of the dialysis fluid before the fluid enters the dialyzer may be advantageously avoided by the fact that according to the present invention the pump is located upstream of the heating device. An undesired cooling might result in deviations of the temperature which are difficult to estimate. According to the present invention such deviations may be avoided while accomplishing the advantages provided by the present invention.

For detecting a vacuum or a negative pressure inside the heating device, for example a bag heater, in order to avoid same, by means of the solution provided by the present invention between the heating device and the dialyzer in a manner according to the present invention it is not required to monitor the filtrate pressure, i.e., the dialysate fluid pressure inside the dialyzer close to the membrane, or another pressure, with regard to a suitable minimum value. For example, there is essentially no relevant flow resistance between the filtrate pressure monitoring and the heating device in an arrangement for continuous veno-venous hemodiafiltration (CW-HDF). Though it would be possible after a correction by a hydrostatic pressure difference to identify a minimum filtrate pressure at which the pressure inside the heating device is for sure sufficiently high to avoid collapsing of the bag. For example, the flow rate of the pump could be decreased when and if the pressure falls below the minimum filtrate pressure. However, to this end a control circuit would be required. This means costs and inconvenience, maintenance, calibration, and the like. According to the present invention, this is not necessary.

Also, such a solution bears the risk that false alarms might occur within the permitted range of flow rates of the pump and that certain treatment parameters are not admissible. Therefore uninterpretable warnings may occur (heating bag running dry, balance warnings, heater alerts). By using the tubing adapter, the minimum filtrate pressure does not have to be monitored.

According to another advantage the pressure inside the bag of the heating device may be increased by the tubing adapter by a required value ranging between 5 and 1000 hPa, preferably between 50 and 400 hPa, particularly preferred between 100 and 350 hPa. This value may be set or is selectable by a known device as mentioned above, such as a valve, based on the opening pressure in the flow direction.

Increasing the pressure in a manner possible according to the present invention, advantageously counteracts or mainly avoids an undesired out-gassing of the solution when being in contact with the warm heating surface as it may happen at a low pressure. Hence, a pH shift caused by the out-gassing and in particularly by the out-gassing of $CO_2$ and, hence, undesired precipitations of calcium-carbonate and other chemical compounds from the flowing solution may be avoided.

According to another advantage of the tubing adapter, the latter may be retrofitted once collapsing of the heating device or the heating bag is identified. This way a costly and complex integration of, for example, a check valve or a pressure stop valve into each of the manufactured dialysis fluid tubing systems may be avoided or waived.

The present invention shall be exemplarily explained hereinafter with reference to the accompanying drawings in which identical reference numerals refer to same or similar elements. The following applies in the partly strongly simplified figures.

DETAILED DESCRIPTION

Figure 1:
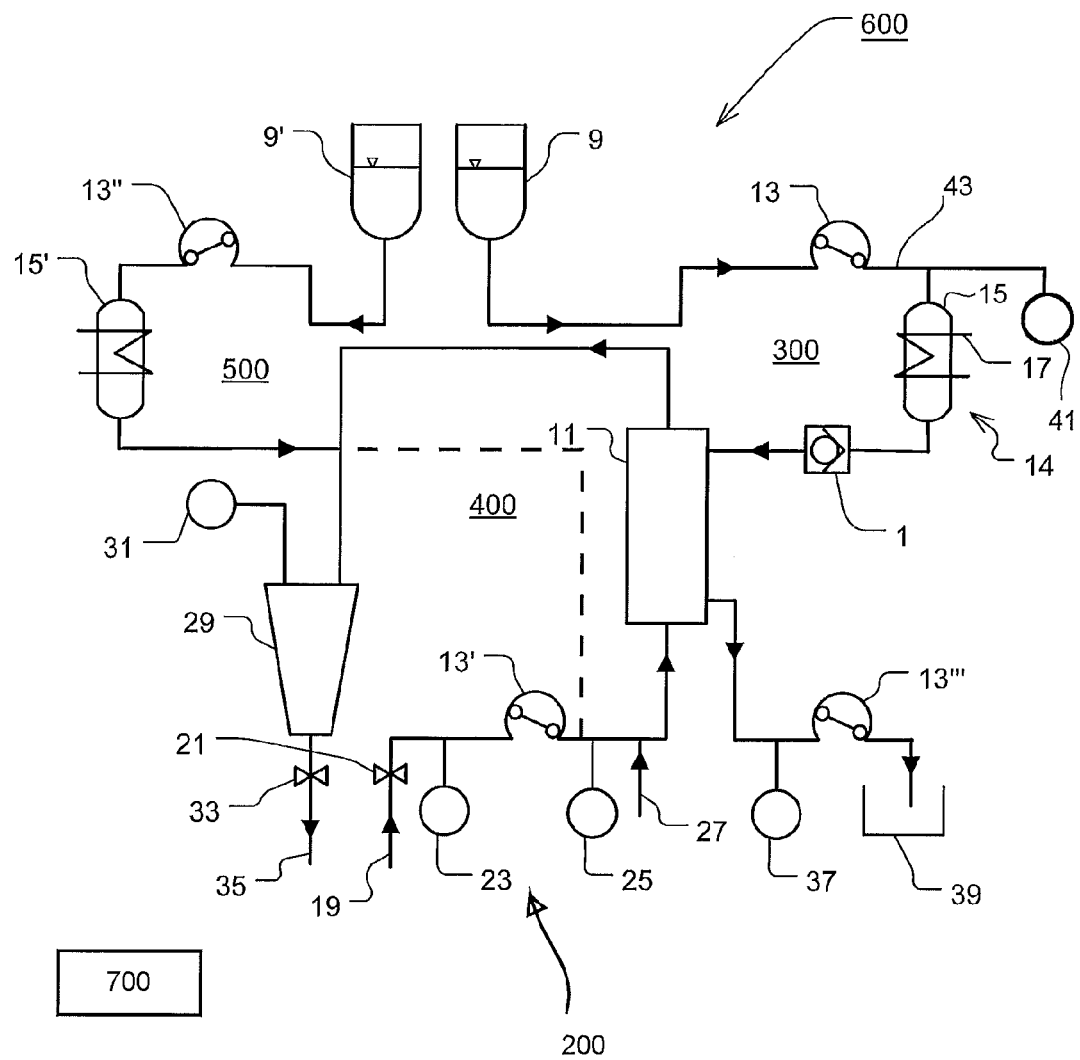
FIG. 1 shows schematically a medical apparatus according to the present invention for the dialysis with or in an extracorporeal blood circuit and a tubing system in a first embodiment.

FIG. 1 shows a tubing system 200 with a dialysis fluid tubing system 300 and a substituate tubing system 500 in a first embodiment as part of a medical apparatus 600 according to the present invention which is herein, purely exemplarily, a treatment system for a dialysis. The medical apparatus 600 further comprises a blood circuit 400 (represented herein as a section), furthermore a dialyzer 11, which is flown by two fluid systems (blood and dialysis fluid) for exchange of substances.

The dialysis fluid tubing system 300 which can be embodied as a single use tubing system (disposable) is being filled with dialysis fluid from a bag 9. The dialysis fluid is conveyed along the dialysis fluid tubing system 300 by a pump 13 which, by way of example only, is embodied as a roller pump. The dialysis fluid from bag 9 may flow into a heating device 14 which is arranged downstream of pump 13, that is, on the pressure side of pump 13, by gravity or by aspiration of the pump, or both. The heating device 14 shown in the figures is—by way of example—embodied as a device comprising at least a heating bag 15 and heating rods or heating spindles 17 for which reason it is herein also called a bag heater. The dialysis fluid is heated inside the heating bag 15. For ensuring that heat is transferred from the heating device 14 or the heating spindles 17 to the heating bag 15 it is helpful or may be even necessary that compared to the atmosphere at least a reference pressure, usually or preferably a positive, preferably determinable, inner pressure of the dialysis fluid prevails inside the heating bag 15. This way, the wall of heating bag 15 nestles or adjusts to the heating spindles 17, this enables or promotes the heat transfer. In other words, herein exemplarily, by a positive inside pressure, a collapsing of the heating bag 15 and a deterioration or interruption of the heat transfer is avoided.

Purely optionally, a valve 1 is arranged further downstream of the pump or dialysis fluid pump 13 and downstream of the heating device 14. In this embodiment example the valve 1 is also integrated into the tubing system 300. Therefore, FIG. 1 shows no tubing adapter, which is also encompassed by the present invention. Valve 1, being integrated as is shown here needs, therefore, no tubing couplings. Alternatively, the valve 1, being part of a tubing adapter, may be interconnected with the tubing system 200.

Valve 1 is arranged within the tubing system 300 such that it closes if the pressure upstream of valve 1, that is between valve 1 and heating device 14 or heating bag 15 is too low. By said closing, it is avoided that a pressure which is too low and which prevails downstream of valve 1 propagates upstream of valve 1 and into the heating bag 15 and possibly results in a negative pressure (related to the atmosphere) or in an inside pressure that is lower than desired. As already discussed above, a positive pressure inside the heating bag 15 is helpful for establishing or securing the desired or expected heat transfer.

In certain exemplary embodiments according to the present invention, the opening pressure is between 5 and 1000 hPa, preferably between 50 and 400 hPa, particularly preferably between 100 and 350 hPa. That is, the inner pressure or inside pressure of the heating bag 15 must be at least as high as this value or must exceed a pressure downstream of the valve by at least this value for the valve 1 to open, if the flow loss occurring in the tubing section between the heating bag 15 and the valve 1 are not taken into account. In other words, the pressure upstream of valve 1 must be at least that high (between 5 am 1000 hPa, preferably between 50 and 400 hPa, particularly preferably between 100 and 350 hPa) or exceed by this value to overcome the opening pressure of valve 1.

A lower pressure downstream of valve 1, and, in consequence, evacuating or sucking dry of the dialysis fluid further upstream up to the heating bag 15 may in practice have several reasons.

The medical device 600 (also referred to as a treatment system) is purely exemplarily embodied for dialysis, in this exemplary embodiment especially embodied for the continuous veno-venous hemodiafiltration (a combination of hemofiltration and hemodialysis), short CVV-HDF.

Blood is taken from the patient by an arterial connector 19 or an arterial line of the extracorporeal blood circuit 400. A stop-cock 21 is arranged downstream of the arterial connector 19. Downstream of the latter the arterial pressure is measured by a pressure sensor 23; further downstream there is a blood pump 13'. Between the blood pump 13' and the connector of the arterial line for connecting the arterial line with the dialyzer 11 the hemofiltration pressure or the pre-filter pressure is measured by a pressure sensor 25. Downstream of the pressure sensor 25 heparin is administered to the blood for anticoagulation at an admission port 27.

Within the dialyzer 11 substances are exchanged with the dialysis fluid of the tubing system 300 which leaves the dialyzer 11 as dialysate. This will be further explained below.

Downstream of the dialyzer 11, the blood flows in a venous drop chamber 29 in which the venous pressure is measured by a pressure sensor 31. A stop-cock 33 is arranged downstream thereof. The blood is returned into the vessels of the patient by a venous connector 35.

The substitute tubing system 500 serves to partly substitute the fluid volume which was removed by filtration or ultrafiltration within the dialyzer 11 during treatment. To this end, substitute fluid from a bag 9' is used. The substitute is conveyed within the substitute tubing system 500 by a substitute pump 13" into a heating bag 15' where it is heated before it is fed into the blood circuit 400.

The dialysis fluid tubing system 300 upstream of the dialyzer 11 has already been explained with reference to FIG. 2. The filtrate pressure is measured downstream of the dialyzer 11 by a pressure sensor 37; further downstream the dialysate is—together with the filtrate—conveyed into a collecting bag 39 by a pump 13''' (referred to also as dialysate or filtrate pump) or disposed.

In the following, reasons for a low pressure downstream of valve 1 are discussed.

A lower pressure (when compared to the atmosphere) downstream of valve 1 which would possibly result in evacuating or sucking dry of the heating bag 15 if there was no valve 1 may be caused by, for example, deposit on the filter membrane of the dialyzer 11 (on the membrane side of the blood circuit 400; for example by blood that starts clotting). This results in a decrease of the permeability of the filter membrane in the dialyzer and also to an increased transmembrane pressure TMP.

Regardless of this phenomenon using filter membranes of low permeability may also result in this low pressure problem on the dialysis side of the dialyzer 11 (the same effect as with deposit on the membrane may occur here). Thus, a low permeability results in a high TMP for achieving a desired or requested exchange of substances in the dialyzer 11. Hence, when using filter membrane having low permeability, the dialysis fluid tubing system 300 may be used in order to avoid a marked negative pressure in the heating bag 15, thus, ensuring an optimal, desired or expected heat transfer from the heating housing to the heating bag 15.

A pressure on the dialysis side which is possibly too low for the needs of the heating bag occurs particularly during dialysis treatments which are performed or executed by means of the continuous veno-venous hemodiafiltration (CW-HDF). In this case, also the substituate volume added by the machine through the substituate tubing system 500 over the filter membrane of the dialyzer 11 must be withdrawn from the patient in addition to the fluid which should be withdrawn from the patient by the dialyzer 11. This requires high filtration flow rates and a correspondingly high pressure gradient over the filter membrane, i.e., a high transmembrane pressure TMP.

The pressure reference point for the area around the filter membrane of the dialyzer 11 is located in the area of the venous connector 35. The pressure reference point for the dialysis side is the pressure sensor 37. From there, the pressure of the dialysis side of the filter membrane (in the dialysis fluid tubing system 300) may be tracked back by considering pressure differences caused by flow and by hydrostatic pressure differences. It is readily understood that with a sufficiently high TMP a pressure below atmosphere may prevail within the heating bag 15 and that the heating bag may collapse if this is not avoided by, for example, using the tubing adapter or the dialysis fluid tubing system 300.

A control or regulating device 700 is indicated in the figures purely schematically. In practice, it is connected in signal communication to the corresponding components such as pressure detectors, ultrafiltration pumps or substituate pumps.

FIG. 1 shows an exemplary arrangement in which the valve 1 is provided. With such an arrangement, the pressure may be—as one possibility out of many for determining the/a pressure—determined by an optionally provided pressure detector 41, which is purely exemplarily arranged in a dialysis fluid line 43.

In case the valve 1 is not provided, then pressure may also be determined by the pressure sensor 37.

Determining the pressure by the pressure detector 41 has the additional advantage that increases of pressure in the heating bag 15 may be recognized or detected. Such increases of pressure may, for example, occur due to a closed clamp which has been unintentionally placed on a dialysate line downstream of the dialyzer 11 or has not been removed off the latter at the beginning of the treatment. Thus, the heating bag 15 may be protected against too-high pressure and therefore against damage, for example by stopping the dialysis fluid pump 13. Such stopping may be carried out automatically. A corresponding alarm may alternatively or additionally be issued. The herein described determining of pressure and the advantages related thereto are also possible or achievable in other sections of the tubing system 200, as it is purely exemplarily shown in FIG. 4 for the substituate tubing system 500 with a pressure detector 45 and a valve 49.

It is pointed out that the embodiments according to the present invention shown in the figures and/or described supra are not at all limited in their use to tubing systems which are used in the dialysis. Each other treatment method may equally profit from the present invention.

In the figures, an addition of substituate in post-dilution (i.e., downstream of the dialyzer 11) is illustrated. The dashed line shows, respectively, that an addition also in pre-dilution (i.e., upstream of the dialyzer 11) is possible and may be provided.

Figure 2:
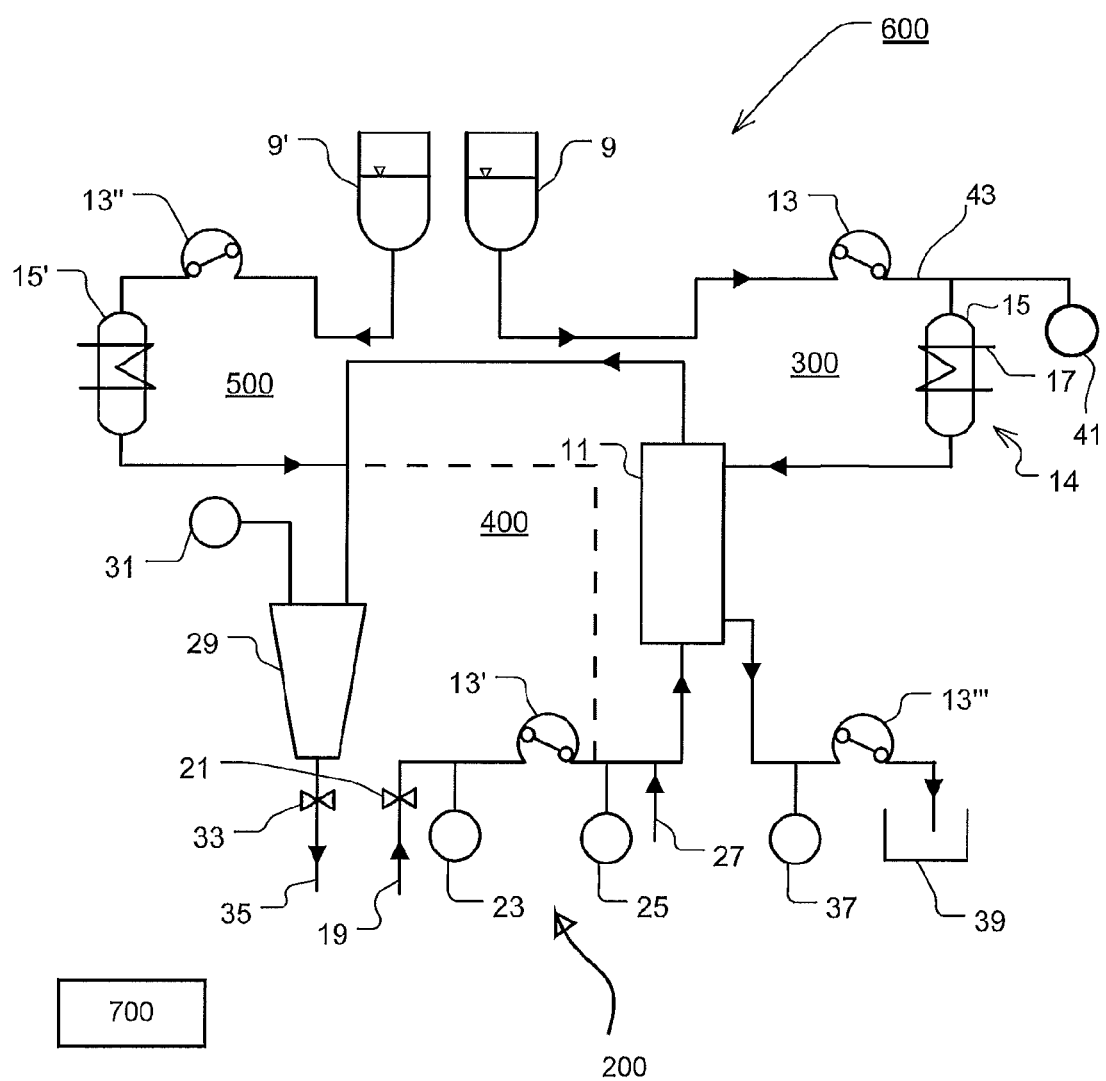
FIG. 2 shows schematically a medical apparatus according to the present invention for the dialysis with or in an extracorporeal blood circuit and a tubing system in a second embodiment.

FIG. 2 shows schematically a medical apparatus according to the present invention with a tubing system in a second embodiment.

In FIG. 2, the dialysis fluid tubing system 300 comprises a pressure detector 41, which is arranged in a dialysis fluid line 43. FIG. 2 does not show the purely optional valve 1 of FIG. 1. Nevertheless, it might also have been provided there.

Figure 3:
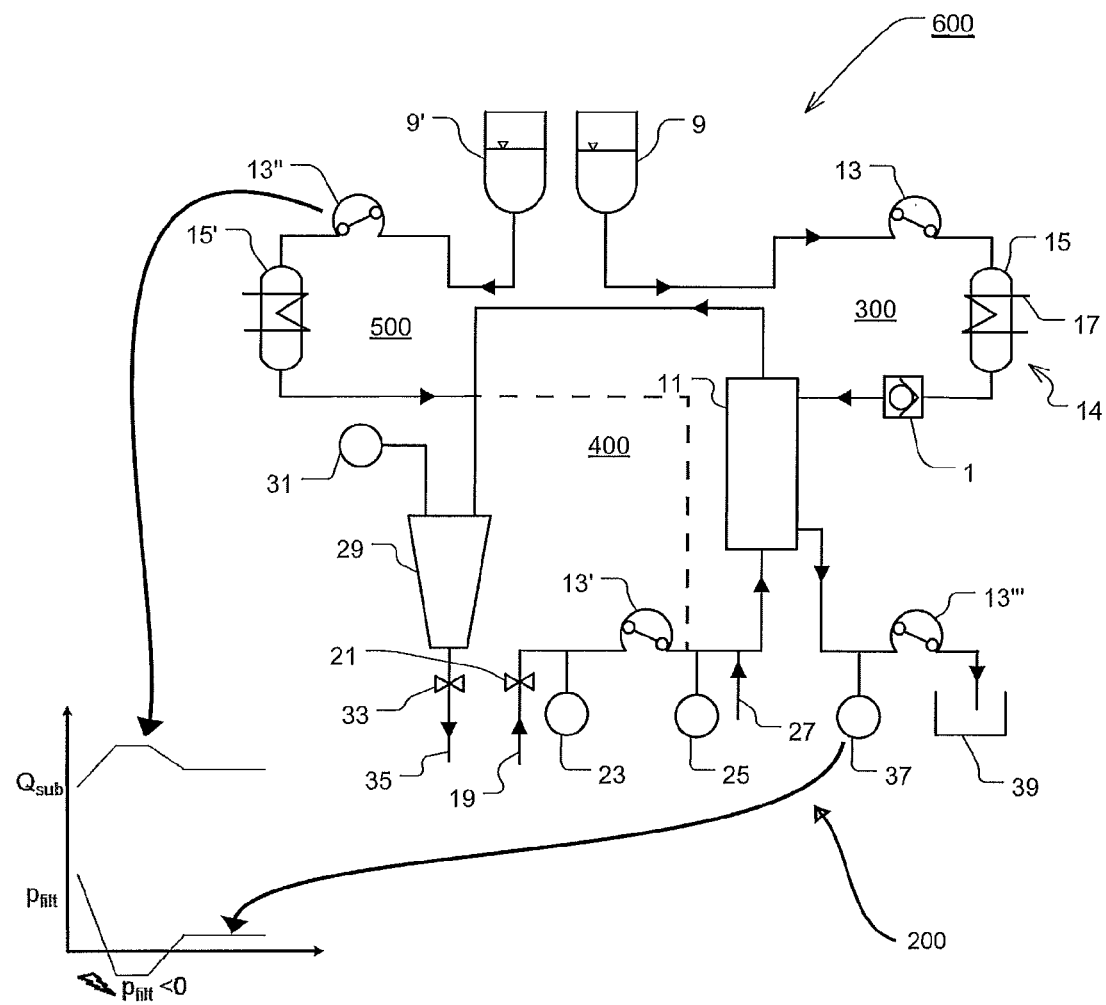
FIG. 3 shows schematically a medical apparatus according to the present invention for the dialysis with or in an extracorporeal blood circuit and a tubing system in a third embodiment.

FIG. 3 shows schematically a medical apparatus according to the present invention with a tubing system in a third embodiment. In FIG. 3, the dialysis fluid tubing system 300 does not comprise the optional pressure detector 41.

FIG. 3 illustrates one of the possible functionalities of the control and regulating device 700. With the regulation shown in FIG. 3, which may also be a controlling, the device 700 is then used to effect the substituate pump 13'', when the pressure sensor 37 detects or determines a pressure downstream of the dialyzer 11, herein the filtrate pressure p_filt, which is, for example, below the reference pressure. Such effect decreases the substituate flow Q_sub, for example during a CVV-HDF treatment, until or such that the filtrate pressure p_filt exceeds or rises above the reference pressure. In the example of FIG. 3, the reference pressure corresponds to the ambient pressure. In case the filtrate pressure p_filt exceeds the reference pressure or ambient pressure again, the heating bag will not collapse (anymore).

It is additionally pointed out that the aforementioned, performed regulation/control is arranged to maintain or keep the adjusted or set total decrease in weight which results from the balance between the weight of the fluid being withdrawn from the patient and the weight of the fluid being given to the patient by substitution untouched or unchanged. In case of a threat of the heating bag 15 collapsing, then the flow rate of the filtrate pump 13''' must be reduced to counteract a collapse. As a result of such decrease, there will be less filtering out of filtrate through the dialyzer membrane. Hence, the rate of the decrease of weight does not correspond to what has been adjusted by the doctor, it is too low. Less fluid as a whole is withdrawn out of the patient than desired. Said fluid is compensated in that the substituate rate is correspondingly reduced as well by the substituate pump 13''. The fluid balance being based on the ultrafiltration rate is thus ensured by reducing both the ultrafiltration and the addition of substituate. This is indicated in FIG. 3 with the arrows.

Figure 4:
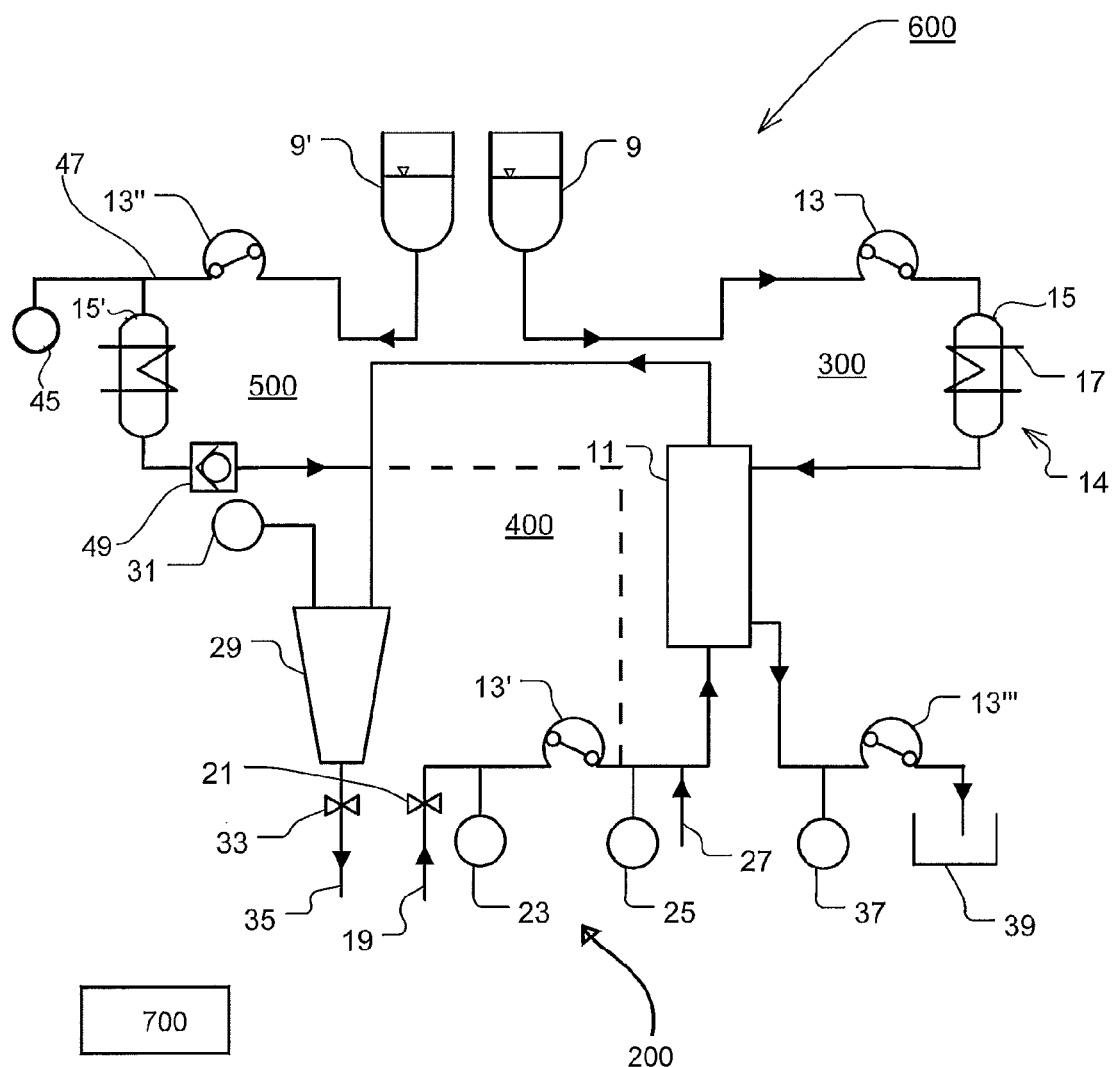
FIG. 4 shows schematically a medical apparatus according to the present invention for the dialysis with or in an extracorporeal blood circuit and a tubing system in a fourth embodiment.

FIG. 4 shows schematically a medical apparatus according to the present invention for the dialysis with one tubing system in a fourth embodiment.

In FIG. 4, there is a likewise purely optional pressure detector 45 of a substituate line 47 downstream of the substituate pump 13'' instead of the optional dialysis fluid line 43. The embodiment of FIG. 4 comprises in addition a valve 49 downstream of the heating bag 15'. Valve 49 may correspond to valve 1 of FIGS. 1 and 3 both in function and in structure.

The provision of the pressure detector 45 advantageously allows a detection of an over pressure or of an inadmissible high pressure in the heating bag 15'. Therefore, it is possible to avoid an explosion of the heating bag 15' by taking appropriate measures like stopping or reducing or decreasing the corresponding pump.

It is pointed out that embodiments according to the present invention may separately comprise a valve 1, a valve 49, a pressure detector 41, a pressure detector 45 and/or a pressure sensor 37. The control or regulating device 700 is suitably configured to respectively influence at least the pumps 13, 13'' or 13''' as well as optionally on the valve 1, 49—when being intentionally adjustable by means of an actuator, e.g., by opening and closing—in order to effect a change of the respective, monitored or detected pressure in a desired range or beyond a threshold.

Figure 5:
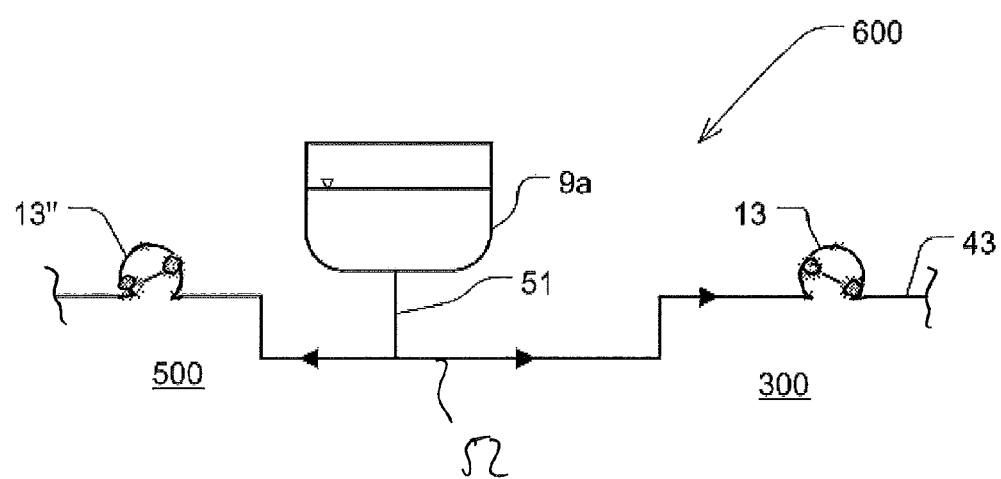
FIG. 5 shows schematically strongly simplified a first development according to the present invention of a section of the medical apparatus.

FIG. 5 shows schematically, strongly simplified a first development according to the present invention of a section of the medical apparatus.

In this embodiment, the containers 9 and 9' of the previous figures are combined to one container 9a. The dialysis fluid pump 13 and the substituate pump 13'' are supplied together by the container 9a, for example through a common line 51.

The design according to the present invention of FIG. 5, which, unlike the designs described in the previous figures, provides a common supply to or towards dialysis fluid pump 13 and substituate 13'' from only, in any case however from one common source, may complement each feature combination or embodiment disclosed herein. Such design is thus combinable with each of the herein made embodiments and may thereby replace the separate supply from separate sources regardless of all other details of the design.

Furthermore, a connecting line 52 between the supply line of the dialysis fluid pump 13 and the supply line of the subsituate pump 13'' is shown in FIG. 5.

Figure 6:
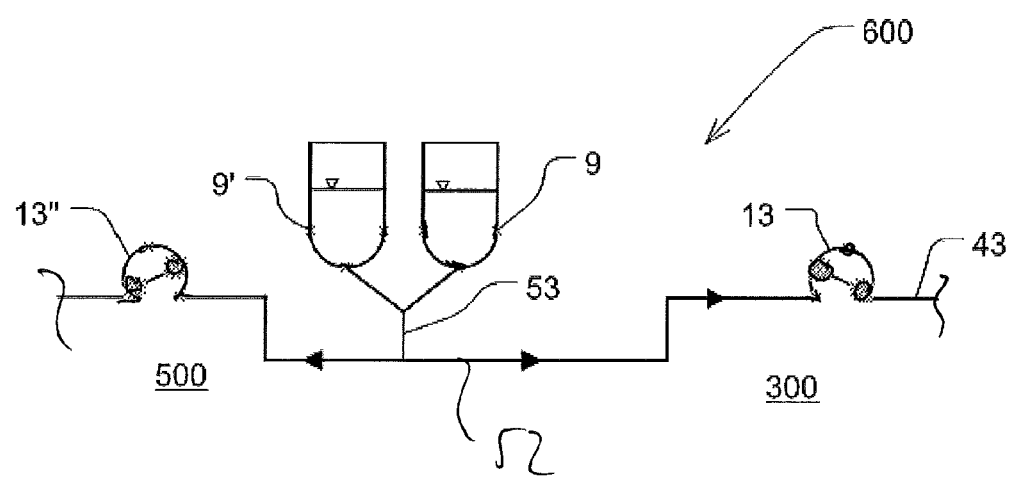
FIG. 6 shows schematically strongly simplified a second development according to the present invention of a section of the medical apparatus.

FIG. 6 shows schematically, strongly simplified a second development according to the present invention of a section of the medical apparatus.

The design according to the present invention of FIG. 6, which, unlike the designs described in the previous figures, provides a Y-piece 53 for the common supply of the dialysis fluid pump 13 and substivate pump 13'', however from separate sources, may as well complement each feature combination or embodiment disclosed herein. Such design is thus combinable with each of the herein made embodiments and may thereby replace the separate supply from separate supply lines regardless of all other details of the design.

In FIGS. 5 and 6 the supply lines for substituate and dialysis fluid are in fluid communication via the connecting line 52. Also this design may likewise complement each feature combination or embodiment disclosed herein, regardless of the other features.

| List of Reference Numerals | |
|---|---|
| Reference | Description |
| 200 | tubing system |
| 300 | dialysis fluid tubing system |
| 400 | blood circuit |
| 500 | subsituate tubing system |
| 600 | medical apparatus |
| 700 | control and regulating device |
| 1 | check valve, valve |
| 9, 9' | bag |
| 9a | container |
| 11 | dialyzer |
| 13 | dialysis fluid pump |

-continued

List of Reference Numerals

| Reference | Description |
|---|---|
| 13' | blood pump |
| 13" | substitute pump |
| 13'" | dialysate pump |
| 14 | heating device |
| 15, 15' | heating bag |
| 17 | heating spindle or coil, heating rods |
| 19 | arterial connector |
| 21 | stop-cock, arterial |
| 23 | arterial pressure sensor |
| 25 | pressure sensor for hemofiltration pressure or pre-filter pressure |
| 27 | admission port for heparin |
| 29 | venous drop chamber |
| 31 | venous pressure sensor |
| 33 | stop-cock, venous |
| 35 | venous connector |
| 37 | pressure sensor for filtrate pressure |
| 39 | collecting container |
| 41 | pressure detector |
| 43 | dialysis fluid line |
| 45 | pressure detector |
| 47 | substituate line |
| 49 | check valve, valve |
| 51 | common line |
| 52 | connecting line between the pumps |
| 53 | Y-piece |

The invention claimed is:

1. A method for regulating or controlling, during a treatment of blood of a patient, a pressure which prevails within a heating bag of a tubing system used for the treatment, the method comprising:
   determining the pressure;
   comparing the determined pressure to a reference pressure or detecting the determined pressure's state with respect to a reference pressure range; and
   avoiding a collapse of the heating bag by changing at least one treatment parameter of the treatment of the patient or suggesting a correction or change of the at least one treatment parameter when the determined pressure is below or above the reference pressure, or is outside of the reference pressure range.

2. The method according to claim 1, wherein determining the pressure is achieved by measuring with or via a pressure sensor.

3. The method according to claim 1, wherein the at least one treatment parameter of the treatment is a substitution flow or an ultrafiltration rate.

4. The method according to claim 2, wherein the at least one treatment parameter of the treatment is a substitution flow or an ultrafiltration rate.

5. The method according to claim 3, wherein the substitution flow is reduced such that or until the determined pressure is above or below the reference pressure, or again reaches within the reference pressure range.

6. The method according to claim 4, wherein the substitution flow is reduced such that or until the determined pressure is above or below the reference pressure, or again reaches within the reference pressure range.

7. The method according to claim 1, wherein the reference pressure is ambient pressure.

8. The method according to claim 5, wherein the reference pressure is ambient pressure.

9. The method according to claim 1, wherein the pressure is determined by a pressure detector arranged in a dialysis fluid line of the tubing system downstream of a dialysis fluid pump.

10. The method according to claim 7, wherein the pressure is determined by a pressure detector arranged in a dialysis fluid line of the tubing system downstream of a dialysis fluid pump.

11. The method according to claim 1, further comprising effecting or manipulating the determined pressure by a device arranged upstream of a dialyzer and downstream of a heating device, wherein the device is a valve, a throttle or an orifice.

12. The method according to claim 7, further comprising effecting or manipulating the determined pressure by a device arranged upstream of a dialyzer and downstream of a heating device, wherein the device is a valve, a throttle or an orifice.

13. The method according to claim 1, wherein the pressure is determined by a pressure detector arranged in a substituate line of the tubing system downstream of a substituate pump.

14. The method according to claim 7, wherein the pressure is determined by a pressure detector arranged in a substituate line of the tubing system downstream of a substituate pump.

15. The method according to claim 1, wherein the heating bag contains dialysis fluid or substituate.

16. The method according to claim 9, wherein the heating bag contains dialysis fluid or substituate.

17. A medical apparatus comprising a control or regulating device for controlling or regulating, during a treatment of blood of a patient, a pressure which prevails within a heating bag of a tubing system used for the treatment, the control or regulating device configured to:
   determine the pressure;
   compare the determined pressure to a reference pressure or detect the determined pressure's state with respect to a reference pressure range; and
   avoid a collapse of the heating bag by changing at least one treatment parameter of the treatment or suggesting a correction or change of the at least one treatment parameter when the determined pressure is below or above the reference pressure, or is outside of the reference pressure range.

18. The medical apparatus according to claim 17, wherein the medical apparatus is a blood purification device or a dialysis device.

19. An extracorporeal blood treatment method comprising:
   determining a pressure within a medical fluid heating bag;
   comparing the determined pressure to a reference pressure or a reference pressure range; and
   avoiding a collapse of the heating bag by changing at least one treatment parameter of the extracorporeal blood treatment method of the patient or suggesting a change of the at least one treatment parameter when the determined pressure is below or above the reference pressure or is outside of the reference pressure range.

* * * * *